(12) United States Patent
Clayton et al.

(10) Patent No.: US 9,486,297 B2
(45) Date of Patent: Nov. 8, 2016

(54) LIGHT FOR ORAL ANESTHESIA INJECTION SYRINGE

(71) Applicants: M. Wade Clayton, Germantown, TN (US); Jimmy E. Brown, Bartlett, TN (US); John Carter McIntyre, Memphis, TN (US)

(72) Inventors: M. Wade Clayton, Germantown, TN (US); Jimmy E. Brown, Bartlett, TN (US); John Carter McIntyre, Memphis, TN (US)

( * ) Notice: Subject to any disclaimer, the term of this patent is extended or adjusted under 35 U.S.C. 154(b) by 0 days.

(21) Appl. No.: 14/341,759

(22) Filed: Jul. 25, 2014

(65) Prior Publication Data
US 2015/0147713 A1 May 28, 2015

Related U.S. Application Data

(63) Continuation-in-part of application No. 14/165,537, filed on Jan. 27, 2014, which is a continuation-in-part of application No. 13/750,111, filed on Jan. 25, 2013, now Pat. No. 8,911,409.

(51) Int. Cl.
*A61C 1/08* (2006.01)
*A61M 5/31* (2006.01)
(Continued)

(52) U.S. Cl.
CPC ............. *A61C 1/088* (2013.01); *A61M 5/24* (2013.01); *A61M 5/3134* (2013.01); *A61M 19/00* (2013.01);
(Continued)

(58) Field of Classification Search
CPC ........ A61B 1/24; A61B 5/0088; A61B 6/14; A61B 19/5202; A61B 2019/521; A61M 5/178; A61M 5/24; A61M 5/3134; A61M 2205/587; A61M 2205/8206; A61M 2005/2407; A61M 5/427; A61M 19/00; A61C 1/088

USPC .......................................................... 433/29
See application file for complete search history.

(56) References Cited

U.S. PATENT DOCUMENTS

| 2,437,697 A | 3/1948 | Kalom |
| 4,040,419 A | 8/1977 | Goldman |

(Continued)

FOREIGN PATENT DOCUMENTS

| DE | 3322923 A1 | 1/1985 |
| DE | 102006018143 | * 10/2007 |

(Continued)

OTHER PUBLICATIONS

International Searching Authority of US PCT Receiving Office, Notification of Transmittal of the International Search Report and the Written Opinion of the International Searching Authority or Declaration, Form PCT/ISA/220 for International Application PCT/US2014/013251 (transmitted May 12, 2014; published Jul. 31, 2014) World Intellectual Property Organization, Geneva, Switzerland.

(Continued)

*Primary Examiner* — Theodore Stigell
(74) *Attorney, Agent, or Firm* — Walker, McKenzie & Walker, P.C.

(57) ABSTRACT

A light for use with an oral anesthesia syringe that is received into a passageway of a barrel of the light. When the syringe is received into a first opening in a proximal end of the barrel's passageway, the needle of the syringe extends through a second opening at the proximal end of the barrel. A plurality of lamps at the distal end of the barrel illuminate the needle, the interior of a patient's mouth, and an injection site of the needle. A battery is included in the light for powering the lamps. Power is selectively applied to the lamps. A circuit may disable illumination after about ten minutes of use.

5 Claims, 8 Drawing Sheets

(51) Int. Cl.
*A61M 5/32* (2006.01)
*A61M 19/00* (2006.01)
*A61M 5/24* (2006.01)
*A61B 1/24* (2006.01)

(52) U.S. Cl.
CPC ......... *A61B 1/24* (2013.01); *A61M 2005/2407* (2013.01); *A61M 2205/587* (2013.01); *A61M 2205/8206* (2013.01); *A61M 2210/0625* (2013.01)

(56) References Cited

U.S. PATENT DOCUMENTS

| | | | |
|---|---|---|---|
| 6,159,161 | A | 12/2000 | Hodosh |
| 6,595,962 | B1 | 7/2003 | Perthu |
| 7,351,231 | B2 | 4/2008 | Young |
| 7,896,838 | B2 | 3/2011 | Devega |
| 8,170,657 | B1 | 5/2012 | Ehrenreich |
| 8,371,848 | B2 | 2/2013 | Okawa et al. |
| 8,613,618 | B2 | 12/2013 | Brokx |
| 8,911,409 | B2 * | 12/2014 | Clayton ............... A61M 5/3134 433/29 |
| 2005/0070848 | A1 | 3/2005 | Kim et al. |
| 2005/0080384 | A1 | 4/2005 | Green, Jr. |
| 2005/0084816 | A1 | 4/2005 | Mehdizadeh |
| 2006/0019220 | A1 | 1/2006 | Loebel |
| 2008/0234625 | A1 | 9/2008 | Dacquay et al. |
| 2009/0093692 | A1 | 4/2009 | Hansma |
| 2009/0216193 | A1 | 8/2009 | Schriver et al. |
| 2010/0069851 | A1 | 3/2010 | Vad et al. |
| 2010/0081919 | A1 | 4/2010 | Hyde |
| 2011/0033817 | A1 | 2/2011 | McKay |
| 2011/0143305 | A1 | 6/2011 | Wagner et al. |
| 2011/0190693 | A1 | 8/2011 | Takatsuka |
| 2013/0203014 | A1 | 8/2013 | Lieb et al. |
| 2014/0316206 | A1 * | 10/2014 | Vasan ................... A61B 1/267 600/191 |

FOREIGN PATENT DOCUMENTS

| | | |
|---|---|---|
| DE | 102006018143 A1 | 10/2007 |
| EP | 0238778 A2 | 9/1987 |
| JP | 2001137341 A | 5/2001 |

OTHER PUBLICATIONS

International Searching Authority of US PCT Receiving Office, International Search Report, Form PCT/ISA/210 for International Application PCT/US2014/013251 (transmitted May 12, 2014; published Jul. 31, 2014) World Intellectual Property Organization, Geneva, Switzerland.

International Searching Authority of US PCT Receiving Office, Search History for International Search Report for International Application PCT/US2014/013251 (transmitted May 12, 2014; published Jul. 31, 2014) World Intellectual Property Organization, Geneva, Switzerland.

International Searching Authority of US PCT Receiving Office, Written Opinion of the International Searching Authority, Form PCT/ISA/237 for International Application PCT/US2014/013251 (transmitted May 12, 2014; published Jul. 31, 2014) World Intellectual Property Organization, Geneva, Switzerland.

Semiconductor Components Industries, LLC, ESD9B, SZESD9B—Transient Voltage Suppressors (Feb. 14, 2014) Semiconductor Components Industries, LLC, Denver, Colorado, U.S.A.

Microchip Technology Inc., MCP65R41/6—3 µA Comparator with Integrated Reference Voltage (Sep. 2011) Microchip Technology Inc., Chandler, Arizona, U.S.A.

International Searching Authority of US PCT Receiving Office, Notification of Transmittal of the International Search Report and the Written Opinion of the International Searching Authority or Declaration, Form PCT/ISA/220 for International Application PCT/US2014/048318 (transmitted Jan. 16, 2015; published Jul. 30, 2015) World Intellectual Property Organization, Geneva, Switzerland.

International Searching Authority of US PCT Receiving Office, International Search Report, Form PCT/ISA/210 for International Application PCT/US2014/048318 (transmitted Jan. 16, 2015; published Jul. 30, 2015) World Intellectual Property Organization, Geneva, Switzerland.

International Searching Authority of US PCT Receiving Office, Search History for International Search Report for International Application PCT/US2014/048318 (transmitted Jan. 16, 2015; published Jul. 30, 2015) World Intellectual Property Organization, Geneva, Switzerland.

International Searching Authority of US PCT Receiving Office, Written Opinion of the International Searching Authority, Form PCT/ISA/237 for International Application PCT/US2014/048318 (transmitted Jan. 16, 2015; published Jul. 30, 2015) World Intellectual Property Organization, Geneva, Switzerland.

* cited by examiner

LIGHT FOR ORAL ANESTHESIA INJECTION SYRINGE

CROSS REFERENCE TO RELATED APPLICATIONS

This application is a continuation-in-part of pending U.S. patent application Ser. No. 14/165,537, filed Jan. 27, 2014, and entitled "Light for Oral Anesthesia Injection Syringe", fully included by reference herein, and claims priority benefit thereof. Said application Ser. No. 14/165,537 was itself a continuation-in-part of U.S. patent application Ser. No. 13/750,111, filed Jan. 25, 2013, and entitled "Light for Oral Anesthesia Injection Syringe", now issued as U.S. Pat. No. 8,911,409 B2 (issued Dec. 16, 2014), fully included by reference herein, of which the instant application also claims priority benefit thereof.

STATEMENT REGARDING FEDERALLY SPONSORED RESEARCH OR DEVELOPMENT

Not applicable.

REFERENCE TO COMPACT DISC(S)

Not applicable.

BACKGROUND OF THE INVENTION

1. Field of the Invention

The present invention relates, in general, to the administration of oral anesthesia into a patient's mouth using a syringe, and, in particular, to lighting of the interior of a patient's mouth during the administration of oral anesthesia.

2. Information Disclosure Statement

Figure 1:
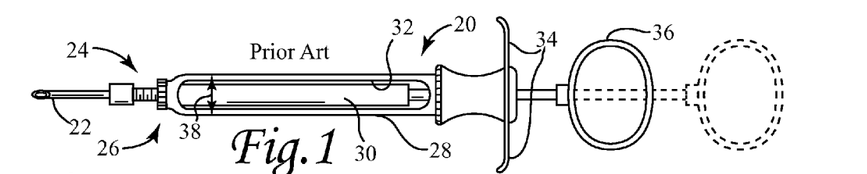
FIG. 1 is a side view of a prior art oral anesthesia injection syringe for use with the present invention.

It is well-known for dentists to use prior art oral anesthesia injection syringes, such as the prior art syringe shown in FIG. 1, to anesthetize a patient's mouth during dental surgery. A problem is that access to the inside of a patient's mouth is limited by the size of the patient's mouth opening, and it is difficult to adequately illuminate the inside of the patient's mouth so that the dentist can view the injection site during application of the anesthesia. Typically a light mounted on a movable arm is used to illuminate the inside of the patient's mouth, but the dentist's head and hands can impede illumination of the inside of the patient's mouth by the light. Also, when the dentist moves to various injection sites inside the patient's mouth, the light on the movable arm may have to be repositioned between injections so as to provide sufficient illumination inside the patient's mouth.

It is therefore desirable to have a light inside the patient's mouth that directly illuminates the desired injection sites as the oral anesthesia injection syringe is moved from one injection site to another. It is further desirable to provide a "hands free" means of lighting the inside of the patient's mouth that moves with the oral anesthesia injection syringe and that does not require an additional hand to manage the positioning of the lighting of the inside of the patient's mouth.

It is further desirable to provide a single-use disposable oral anesthesia injection syringe that illuminates the inside of a patient's mouth.

Furthermore, in a single use battery powered device such as an LED flashlight, once the light is activated, the battery begins to discharge and the LED emits less and less usable illumination with time. At some point, the light is too dim to be useful, and, for a single use device without an off switch, the LED would continue to glow dimmer and dimmer, likely for days after being discarded from use. It is desirable to incorporate a shut off device that would extinguish the LED completely at some diminishing point of its useful illumination, rather than allow it to glow ever more dimly for days until extinction.

Various battery technologies each have their own specific discharge characteristics. Some source current at relatively steady rates while their voltage decreases with time, while others may maintain a fairly steady voltage through their discharge curve as their ability to source current decreases with time. Because batteries utilize chemical reactions to generate power, they tend to exhibit a small amount of recovery in their output voltage and current capacity over time after being disconnected from their load. It is this small recovery characteristic which makes basic voltage or current sensing switches employed to disconnect, or turn off a load, tend to oscillate at a very low rate, or switch on and off again and again.

If a basic voltage or current sensing switch with typical hysteresis were used in the case of a single use flashlight, once the light became too dim to be useful, the switch would shut the light off and it would likely be set aside or perhaps discarded in the trash. Once disconnected from the load, the batteries would experience some recovery in their voltage and current capacity with time and turn the switch and the light on again. The batteries would then deplete again with time and switch off again after this. In essence, the light would blink on and off, again and again, as the batteries cycle through depletion and recovery cycles over and over. This cyclic process could continue for days until the batteries were finally depleted beyond their ability to generate visible illumination.

It is therefore desirable to utilize a device that would prevent this cyclic blinking behavior and positively extinguish the light permanently once it had gone dim past the point of useful illumination.

It is still further desirable to provide a single-use disposable oral anesthesia injection syringe that illuminates the inside of a patient's mouth, in which the illumination self-extinguishes after approximately ten minutes of use so that the apparatus may be discarded into a disposal container for hazardous biological materials without illuminating the disposal container.

BRIEF SUMMARY OF THE INVENTION

The present invention is a light for use with an oral anesthesia syringe that is received into a passageway of a barrel of the light. When the syringe is received into a first opening in a proximal end of the barrel's passageway, the needle of the syringe extends through a second opening at the proximal end of the barrel. At least one lamp and preferably a plurality of lamps at the distal end of the barrel illuminate the needle and the interior of a patient's mouth. A battery is provided in the light for powering the lamps. The insertion of the syringe into the barrel closes a pair of contacts to cause the battery to power the lamps, or an insulating strip may be pullingly removed when the device is used so that the battery may be connected into the circuit so as to power the lamps. To turn the lamps off, the battery may be removed in order to remove power from the lamps.

Preferably, an electrical circuit of the present invention can automatically cut off and extinguish power to the lamps after a certain time, about ten minutes, while draining the power from the battery so that it cannot recover and re-illuminate the lamps.

It is an object of the present invention to provide illumination of the needle of an oral anesthesia syringe and of the anesthesia injection site within a patient's mouth. It is a further object of the invention to provide self-contained "hands free" illumination within the patient's mouth that moves together with the anesthesia syringe, without having cords or wires that extend out of the patient's mouth to an external power source.

Its is a further object of the present invention to provide a single-use disposable oral anesthesia injection syringe that illuminates the inside of a patient's mouth.

It is still further desirable to provide a single-use disposable oral anesthesia injection syringe that illuminates the inside of a patient's mouth, in which the illumination self-extinguishes after approximately ten minutes of use so that the apparatus may be discarded into a disposal container for hazardous biological materials without illuminating the disposal container.

DETAILED DESCRIPTION OF THE INVENTION

FIG. 1 shows a typical well-known prior art oral anesthesia syringe 20 such as would be used with the present invention. A suitable oral anesthesia injection syringe for use with the present invention is the well-known oral anesthesia injection syringe sold by Patterson Dental Supply, Inc., 1031 Mendota Heights Rd., St. Paul, Minn. 55120, U.S.A. The syringe 20 typically has a hypodermic needle 22 that is threadedly received onto a fitting 24 at the front or distal end 26 of the tubular body 28 of the syringe 20. A glass vial 30 of a local anesthetic is received into the body 28, and elongated side openings 32 are provided in the body 28 so that the amount of anesthetic within vial 30 can be observed. Finger grips 34 are provided for the dentist's fingers, and a thumb-operated plunger 36 is pushed into the vial 30 to cause injection of the anesthetic through the hypodermic needle 22, with an outer position of plunger 36 being shown in dotted outline. The parts of syringe 20 are typically made of stainless steel so that the syringe 20 may be sterilized in an autoclave. The tubular body 28 of the syringe 20 has a certain body outer diameter 38, typically about 10 mm.

Figures 2, 3, 4, 5, 6, 7, 8, 9, 10:
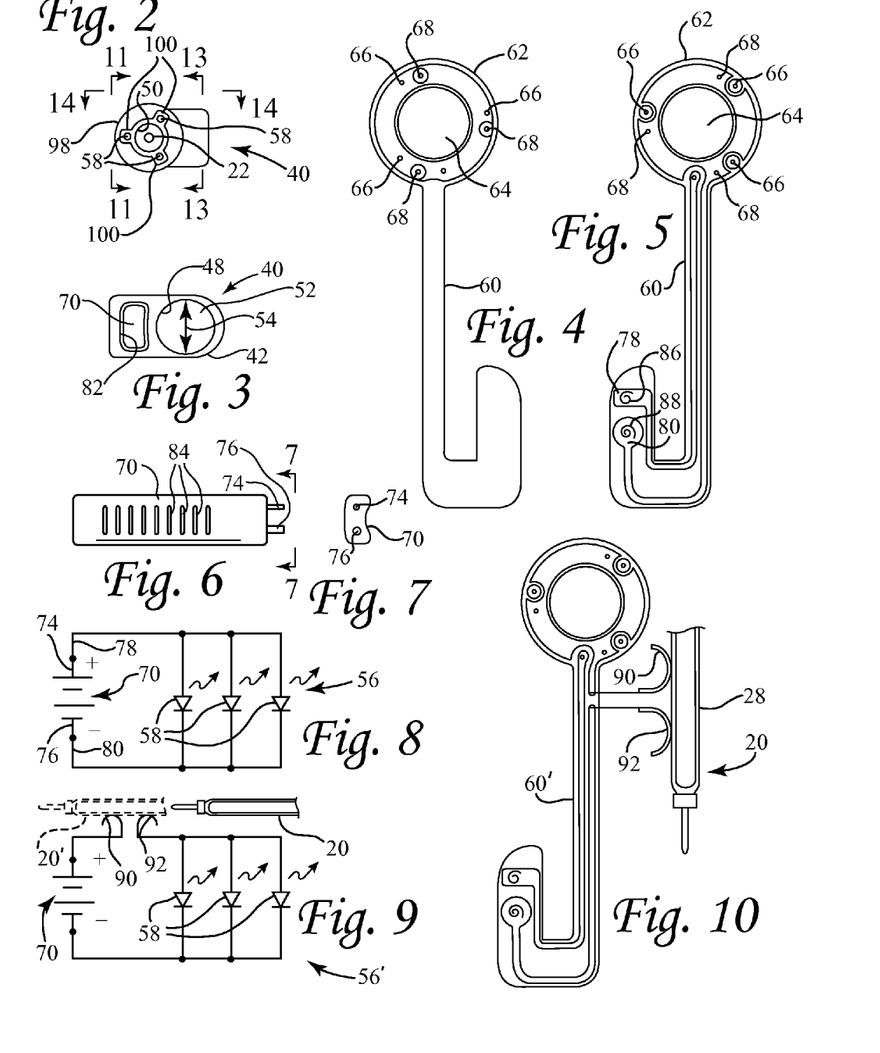
FIG. 2 is a front view of the distal end of the present invention.
FIG. 3 rear view of the proximal end of the present invention with the battery inserted.
FIG. 4 is a plan view of a first side of the first embodiment of the flexible circuitry of the present invention.
FIG. 5 is a plan view of a second side of the first embodiment of the flexible circuitry of the present invention.
FIG. 6 is a side view of the battery of the present invention, removed from the battery compartment.
FIG. 7 is an end view of the battery of the present invention showing the battery contacts, taken substantially along the line 7-7 shown in FIG. 6.
FIG. 8 is a schematic of the present invention using the first embodiment of the flexible circuitry.
FIG. 9 is a schematic of the present invention using the second embodiment of the flexible circuitry, showing the circuit being completed by the metal barrel of the oral anesthesia injection syringe.
FIG. 10 is a plan view of the second side of the second embodiment of the flexible circuitry of the present invention, showing the circuit being completed by the metal barrel of the oral anesthesia injection syringe.
Figure 11:
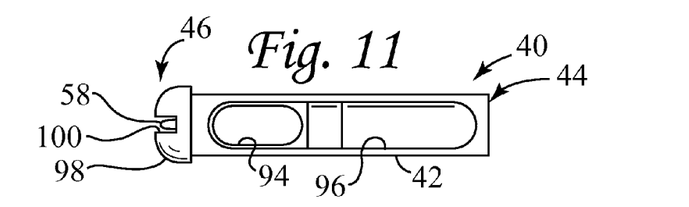
FIG. 11 is a bottom view of the present invention, taken substantially along the line 11-11 shown in FIG. 2.

FIGS. 2-15 of the drawings show the structure of the light 40 of the first preferred embodiment of the present invention, with FIGS. 9 and 10 showing an alternate embodiment, described hereinbelow, of the circuitry.

Figure 12:
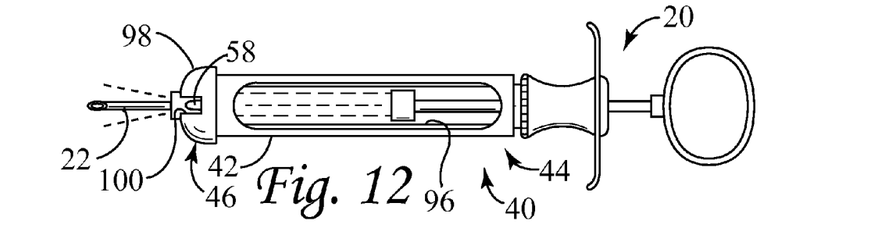
FIG. 12 is another bottom view of the present invention, similar to FIG. 11 but with the oral anesthesia injection syringe being inserted therewithin for use in combination with the present invention.
Figure 13:
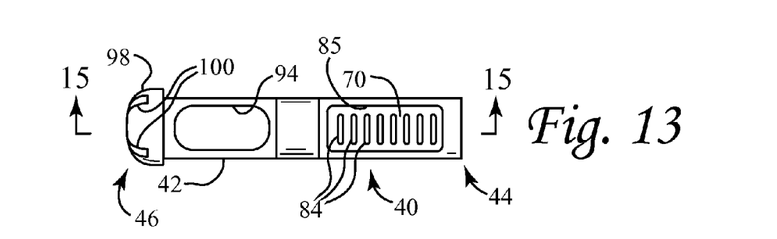
FIG. 13 is top view of the present invention, taken substantially along the line 13-13 shown in FIG. 2.
Figure 14:
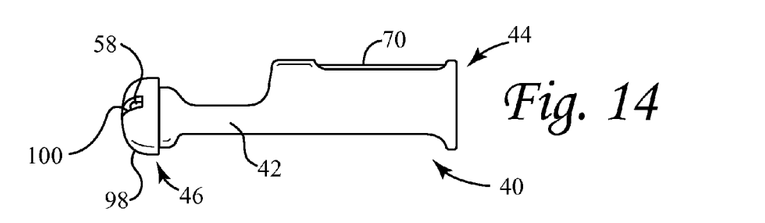
FIG. 14 is side view of the present invention, taken substantially along the line 14-14 shown in FIG. 2. The view from the other side is substantially a mirror image of FIG. 14.
Figure 15:
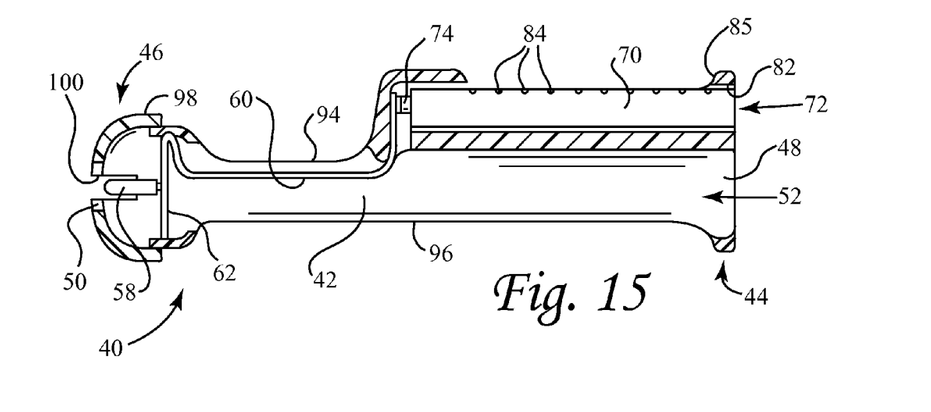
FIG. 15 is a side sectional view of the present invention showing the internal structure, taken substantially along the line 15-15 shown in FIG. 13.

Light 40 includes a barrel 42 having a proximal end 44 and a distal end 46, and barrel 42 has a first opening 48 at proximal end 44 and a second opening 50 at distal end 46. Barrel 42 further has a longitudinal passageway 52 therethrough from first opening 48 to second opening 50, with passageway 52 having a transverse inner diameter 54 larger than the certain body outer diameter 38, for closely receiving the tubular body 28 of syringe 20 therewithin, with the tubular body 28 of syringe 20 extending through the first opening 48 and with the needle 22 extending out of the second opening 50 as best seen in FIG. 12. Preferably the transverse inner diameter 54 is about 1 mm or so larger than the certain body outer diameter 38 so that the syringe 20 will be frictionally retained within the passageway 52 of light 40. It will be understood that first opening 48, second opening 50, and passageway 52 are preferably co-axial on the longitudinal axis of barrel 42.

Light 40 further includes an electrical circuit 56 including at least one lamp 58 and preferably a plurality of lamps 58, such as the three light emitting diode ("LED") lamps shown in the preferred embodiments of light 40, proximate the distal end 46 of barrel 42, preferably encircling second opening 50 so as to fully illuminate the needle 22 and the anesthesia injection site in the patient's mouth. Electrical circuit 56 preferably includes a printed circuit pattern on a piece of flexible mylar 60 having a ring 62 with a center hole 64 to allow the needle of the syringe 22 to pass therethrough. Each lamp 58 is respectively mounted within a pair of holes 66, 68 in ring 62 that complete the circuit to a battery 70. Battery 70 is preferably rechargeable, as by putting battery 70 in a well-known battery charger, and is received in a battery compartment 72 of barrel 42. Battery 70 has a pair of contacts 74, 76 that contactingly and matingly engage contacts 78, 80 on the mylar circuitry. Battery 70 is preferably asymmetrically shaped to match the opening 82 of compartment 72 so that battery 70 can only be inserted correctly into compartment 72, and a plurality of small transverse channels 84 are preferably provided on an outer surface of battery 70 for ease of removal of the battery 70 as by engaging channels 84 with a user's fingernail through an access opening 85 into battery compartment 72. If desired, contacts 78, 80 on the mylar circuitry may be provided with springs 86, 88 to provide better contact with contacts 74, 76 of battery 70.

In the first embodiment 56 of the electrical circuit, power is applied to lamps 58 when the battery 70 is inserted into the battery compartment 72, thereby completing the circuit as battery contacts 74, 76 connectingly engage with contacts 78, 80 on the mylar circuitry. Likewise, power is removed from lamps 58 when the battery 70 is removed from the battery compartment 72.

An alternate or second embodiment 56' of the electrical circuit is shown in FIGS. 9 and 10, in which a modified version 60' of the mylar circuitry is used. It shall be understood that many aspects of the two preferred embodiments of the electrical circuits 60, 60' are substantially the same, and only the differences will be treated in detail, it being understood that similar structural features of the two embodiments perform similar functions.

In the second embodiment 56' of the electrical circuit, the electrical circuit 56' includes a pair of contacts 90, 92, preferably leaf spring contacts as shown, interposed between battery 70 and lamps 58. Contacts 90, 92 have a first condition, when the tubular body 28 of syringe 20 is not received within passageway 52, in which there is no electrical continuity between contacts 90, 92 (see solid outline of syringe 20 in FIG. 9), and a second condition, when the tubular body 28 of syringe 20 is received within passageway 52 (see dotted outline of syringe 20' in FIG. 9, and solid outline of syringe 20 in FIG. 10), in which there is caused to be electrical continuity between contacts 90, 92. Preferably this second condition of electrical continuity is made by the metal of tubular body 28 of syringe 20 completing the circuit between contacts 90, 92 and causing current to flow between contacts 90 and 92 through the conducting metal of tubular body 28, but the electrical continuity may be caused by mechanical engagement of tubular body 28 with one or both of contacts 90, 92 so as to cause contacts 90 and 92 to directly engage each other for current flow therebetween.

Preferably, the barrel 42 may include one or more elongated viewing openings 94, 96 so that the amount of anesthetic within vial 30 of syringe 20 can be observed during administration of local anesthesia to the patient. A cap 98 is preferably included at the distal end 46 of barrel 42 with there being a slot 100 in cap 98 in alignment with each lamp 58 to allow illumination from lamps 58 to pass to the anesthesia site and to the needle 22. Light 40 is preferably constructed of materials allowing disinfecting of the light before and after use.

To use the light of the first preferred embodiment of the present invention, the battery 70 is first charged in a well-known battery charger and then is inserted into the battery compartment 72. The hypodermic needle 22 is threadedly received onto fitting 24, and a vial 30 of anesthetic is placed within the syringe 20, and the syringe 20 is then inserted into and received within the passageway 52 of the light 40, with the tubular body 28 of the syringe 20 extending through the first opening 48 and with hypodermic needle 22 extending out of second opening 50. The lamps 58 will illuminate the needle 22 and the anesthesia injection site within the patient's mouth as the syringe 20 is used.

FIGS. 16-24 show a second preferred embodiment of an oral injection syringe 2.40 of the present invention, in which the syringe and the light are provided as an integrated unit. FIGS. 26-33 show a third preferred embodiment of the light 3.40 of the present invention. Like the first preferred embodiment 40 of the light of the present invention, the third embodiment light 3.40 of the present invention is used with a typical well-known prior art oral anesthesia syringe 20 as previously described in connection with the first embodiment light 40 and as shown in FIG. 1.

The construction of the second preferred embodiment 2.40 permits the syringe with light combination 2.40 to be provided pre-sterilized in a sealed sterile package that is opened when the syringe is needed to be used. Such a syringe and light combination 2.40 permits the syringe and light combination to be disposed after the single use, thereby reducing or eliminating the possibility of contamination from patient to patient of germs that are difficult if not impossible to kill by standard autoclave or chemical sterilization practices. While the syringe and light combination of the present invention could be sterilized by standard autoclave or chemical sterilization procedures, the inexpensive construction of the syringe and light combination of the present invention permits greater patient safety at minimal cost by having the syringe and light combination 2.40 be disposable and single use. Identifying reference designators for the second preferred embodiment 2.40 of the invention and the third preferred embodiment 3.40 of the present invention and the fourth preferred embodiment 4.40 are marked similarly to the first embodiment, with the reference designators for the second preferred embodiment having a prefix of "2." and with the reference designators for the third preferred embodiment having a prefix of "3." and with the reference designators for the fourth embodiment having a prefix of "4.", and with similar structural features of the first, second, third, and fourth embodiments having the same suffix (e.g., "40", "2.40", "3.40", "4.40", etc.). It shall be understood that many aspects of the three preferred embodiments are substantially the same, and only the differences will be treated in detail, it being understood that similar structural features of the various embodiments perform similar functions.

Syringe with light combination 2.40 includes a body 2.28 having a proximal end 2.44 and a distal end 2.46, with distal end 2.46 being adapted, as by threaded fitting 2.24, for receipt of a hypodermic needle 2.22. As with all embodiments, the syringe body 2.28 receives therewithin a vial 30 of local anesthetic. Just as with prior art oral anesthesia syringes, embodiment 2.40 includes a thumb-operated plunger 2.36 that has a barb 2.37 that is engagingly pushed into the rubber plug 31 of anesthesia vial 30.

Figure 25:
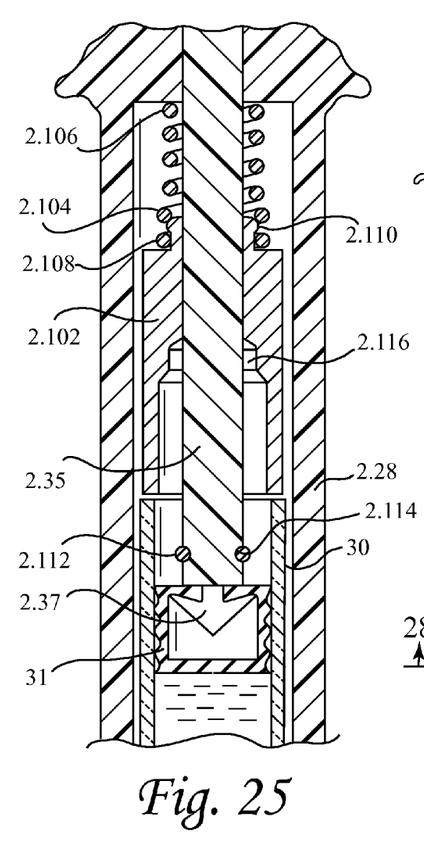
FIG. 25 is a partial sectional view of the second preferred embodiment of the oral injection syringe of the present invention, showing details of the cylindrically-symmetric sleeve, spring, and barbed shaft of the plunger, taken substantially along the line 25-25 shown in FIG. 18.

Syringe with light combination 2.40 also preferably includes a collet or cylindrically-symmetric sleeve 2.102 and compression spring 2.104 mounted upon the shaft 2.35 of plunger 2.36, as best seen in FIG. 25. Compression spring 2.104 preferably tapers from an outer diameter of about 8.8 mm at its proximal end 2.106 to an outer diameter of about 9.75 mm at its distal end 2.108, and distal end 2.108 engages with and is held by a nipple 2.110 of sleeve 2.102. Preferably one "dead" coil at the proximal end 2.106 of spring 2.104 and two "dead" coils at the distal end 2.108 of spring 2.104, and spring 2.104 preferably has a compression force of about 70 g/mm. The purpose of spring 2.104 and sleeve 2.102 is to retain vial 30 within the syringe body 2.28 as best seen in FIG. 25. An encircling wire clip 2.112, received in circumferential groove 2.114 of shaft 2.35, retains spring 2.104 and sleeve 2.102 on shaft 2.35 when anesthesia vial 30 is not present. After the anesthesia has been administered, plunger 2.36 can be retracted, such that wire clip 2.112 will engage with the narrowed bore 2.116 of sleeve 2.102, thereby retracting sleeve 2.102 against compression spring 2.104 as barb 2.37 disengages from plug 31, thereby allowing the used anesthesia vial 30 to be removed.

Figures 16, 17, 18, 19, 20:
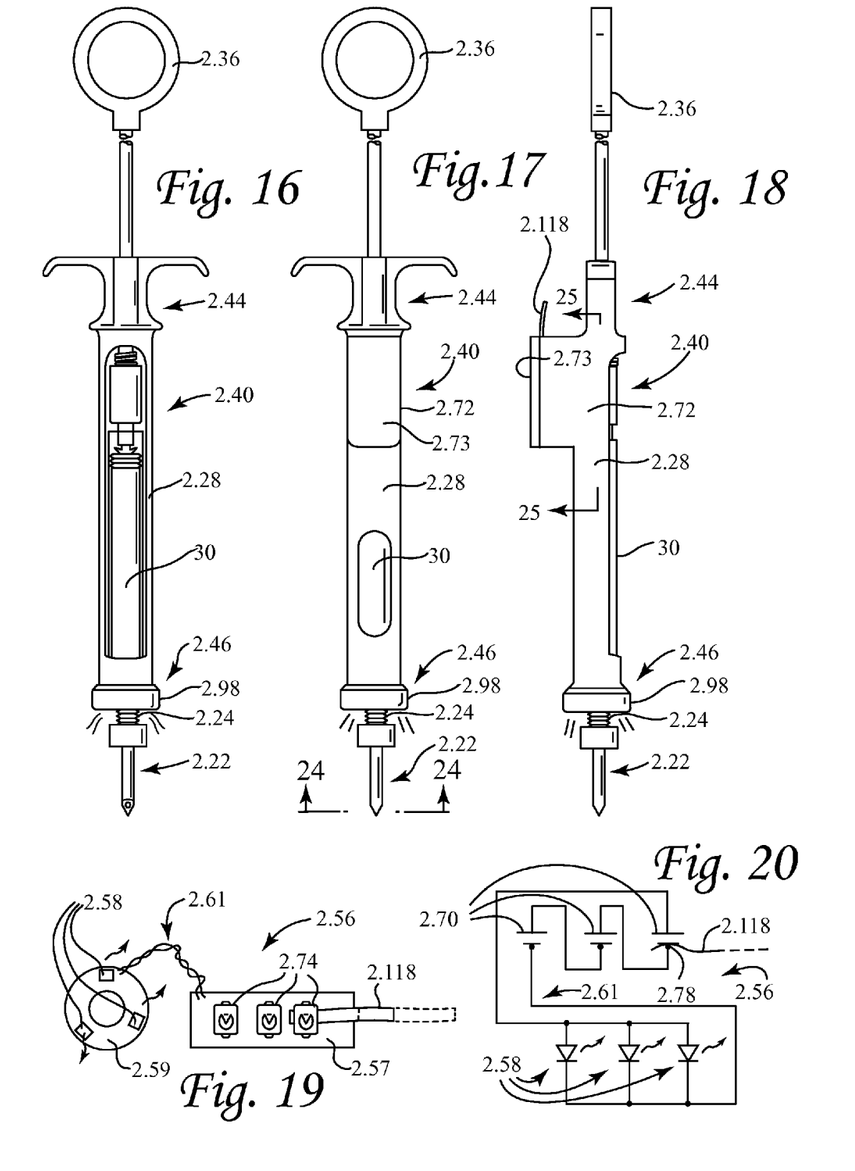
FIG. 16 shows a bottom view of a second preferred embodiment of the oral injection syringe of the present invention that is disposable and single-use.
FIG. 17 shows a top view of the second preferred embodiment of the oral injection syringe of the present invention.
FIG. 18 shows a side view of the second preferred embodiment of the oral injection syringe of the present invention, taken substantially along the line 18-18 shown in FIG. 17. The view from the other side is substantially a mirror image of FIG. 18.
FIG. 19 shows the power circuit board with batteries of the second preferred embodiment of the oral injection syringe of the present invention connected by wires to its LED assembly circuit board, and showing in dotted outline the removal of the insulating strip to apply power to the LED lights.
FIG. 20 shows a schematic of the second preferred embodiment of the oral injection syringe of the present invention and showing in dotted outline the removal of the insulating strip to apply power to the LED lights.
Figure 21:
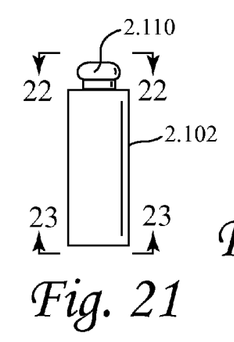
FIG. 21 is a side view of the cylindrically-symmetric sleeve of the second preferred embodiment of the oral injection syringe of the present invention. The view from all sides is the same.
Figures 22, 23:
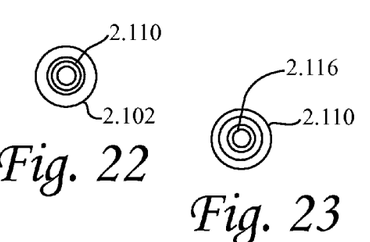
FIG. 22 is a rear view of the cylindrically-symmetric sleeve, taken substantially along the line 22-22 shown in FIG. 21.
FIG. 23 is a front view of the cylindrically-symmetric sleeve, taken substantially along the line 23-23 shown in FIG. 21.
Figure 24:
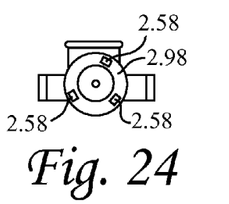
FIG. 24 is a front view of the second preferred embodiment of the oral injection syringe of the present invention, taken substantially along the line 24-24 shown in FIG. 17.

Syringe with light combination 2.40 includes an electrical circuit 2.56 integral with syringe and light combination 2.40, including at least one lamp 2.58 and preferably three lamps 2.58. Electrical circuit 2.56 preferably includes a first circuit board 2.57 and a second circuit board 2.59, interconnected by wires 2.61. Mounted to first circuit board 2.57 are one or more batteries 2.70, each within a well-known battery holder 2.74. Preferably at least one of batteries 2.70 completes its circuit through a contacting plated-through hole 2.78 on circuit board 2.57, and an insulating strip 2.118 is interposed between plated-through hole 2.78 and battery 2.70, thereby interrupting the contact to battery 2.70. When circuit board 2.57 is mounted into battery compartment 2.72, plated-through hole 2.78 is exposed and insulating strip 2.118 is left hanging outside the battery compartment 2.72, as best seen in FIG. 18. To test the operation of electrical circuit 2.56, a conducting (metallic) needle is inserted through plated-through hole 2.78 and through insulating strip 2.118 to battery 2.70, thereby completing the circuit between battery 2.70 and plated-through hole 2.78, thereby causing lamps 2.58 to illuminate for testing during manufacture. Removal of the test needle again causes battery 2.70 to be insulated from plated-through hole 2.78 by insulating strip 2.118, and the top or cover 2.73 of battery compartment 2.72 is closed with insulating strip 2.118 extending outside of battery compartment 2.72, again as best seen in FIG. 18.

To illuminate the lamps 2.58 during normal use by a dentist, the dentist simply pulls the insulating strip 2.118 from the battery compartment 2.72 (see dotted lines in FIGS. 19 and 20), thereby permitting plated-through hole 2.78 to contact battery 2.70, thereby completing the circuit and causing the battery to power lamps 2.58. Insulating strip 2.118 is thus seen to function as a single-use switch to turn the lamps on during use.

Second circuit board 2.59 is mounted to distal end 2.46 of body 2.28, and a transparent cap 2.98 covers circuit board 2.59 and lamps 2.58, and lamps 2.58 shine through transparent cap 2.98.

With the exception of spring 2.104, electrical circuit 2.56, and wire clip 2.112, all parts of second embodiment 2.40 are preferably constructed of a sterilizable plastic so that second embodiment 2.40 can be sterilized, enclosed in a sterile package, opened by the dentist and used, and then discarded after use on a single patient, thereby reducing transmission of germs and diseases between patients. The dentist uses the second embodiment to administer anesthetic just as with the first embodiment.

Improvements have been made to the third preferred embodiment light 3.40, hereinafter described, that provide for ease of construction and assembly as compared to the first preferred embodiment, and the third preferred embodiment light 3.40 is disposable so that it can be pre-sterilized and provided in a sealed sterile package that is opened when the syringe is needed to be used, and then the third preferred embodiment light 3.40 can be disposed of after its single use. Additionally, because the third preferred embodiment is used with a well-known oral injection syringe that has already been approved by governmental approval bodies for use in dentistry with patients, regulatory approval is not required for the third preferred embodiment light 3.40 that attaches to the already-approved oral injection syringe. Otherwise, the third embodiment has many similarities to the first and second embodiments.

Figure 26:
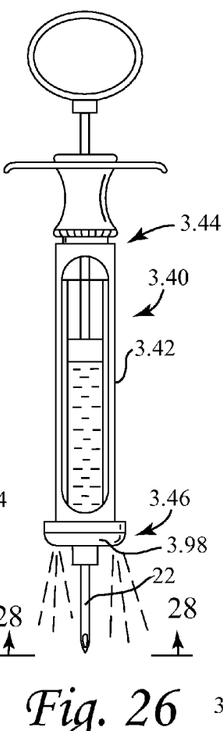
FIG. 26 is a bottom view of the third embodiment of the light of the present invention with the oral anesthesia injection syringe being inserted therewithin for use in combination with the third embodiment.
Figure 27:
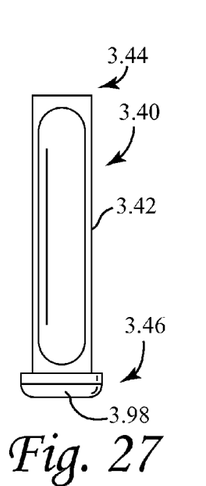
FIG. 27 is another bottom view of the third embodiment of the light of the present invention, similar to FIG. 26 but without the oral anesthesia injection syringe being inserted.
Figure 28:
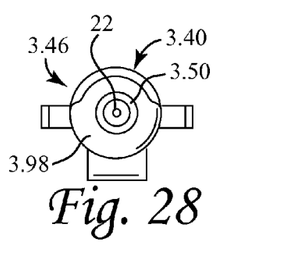
FIG. 28 is a front view of the third embodiment of the light of the present invention, taken substantially along the line 28-28 shown in FIG. 26.
Figure 29:
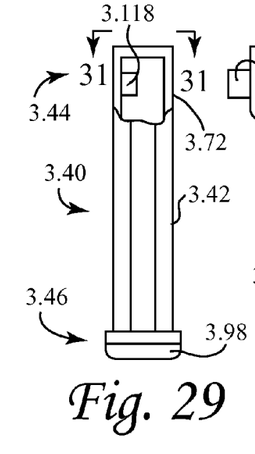
FIG. 29 is a top view of the third preferred embodiment of the light of the present invention without the oral anesthesia injection syringe being inserted.
Figures 30, 31, 32:
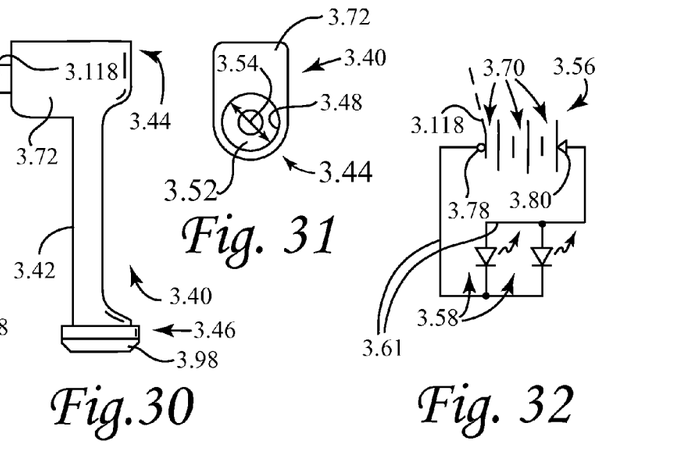
FIG. 30 is a side view of the third preferred embodiment of the light of the present invention without the oral anesthesia injection syringe being inserted. The view from the other side is substantially a mirror image of FIG. 30.
FIG. 31 is a rear view of the third preferred embodiment of the light of the present invention without the oral anesthesia injection syringe being inserted, taken substantially along the line 31-31 shown in FIG. 29.
FIG. 32 is a schematic of the third preferred embodiment of the light of the present invention, showing in dotted outline the removal of the insulating strip to apply power to the LED lights.

Light 3.40 includes a barrel 3.42 having a proximal end 3.44 and a distal end 3.46, and barrel 3.42 has a first opening 3.48 at proximal end 3.44 and a second opening 3.50 at distal end 3.46. Barrel 3.42 further has a longitudinal passageway 3.52 therethrough from first opening 3.48 to second opening 3.50, with passageway 3.52 having a transverse inner diameter 3.54 larger than the certain body outer diameter 38, for closely receiving the tubular body 28 of syringe 20 therewithin, with the tubular body 28 of syringe 20 extending through the first opening 3.48 and with the needle 22 extending out of the second opening 3.50 as best seen in FIGS. 26 and 28. Preferably the transverse inner diameter 3.54 is about 1 mm or so larger than the certain body outer diameter 38 so that the syringe 20 will be frictionally retained within the passageway 3.52 of light 3.40. It will be understood that first opening 3.48, second opening 3.50, and passageway 3.52 are preferably co-axial on the longitudinal axis of barrel 3.42.

Light 3.40 further includes an electrical circuit 3.56 including at least one lamp 3.58 and preferably a plurality of lamps 3.58, such as the two light emitting diode ("LED") lamps shown in the preferred embodiments of light 3.40, proximate the distal end 3.46 of barrel 3.42, preferably around second opening 3.50 so as to fully illuminate the needle 22 and the anesthesia injection site in the patient's mouth.

Figure 33:
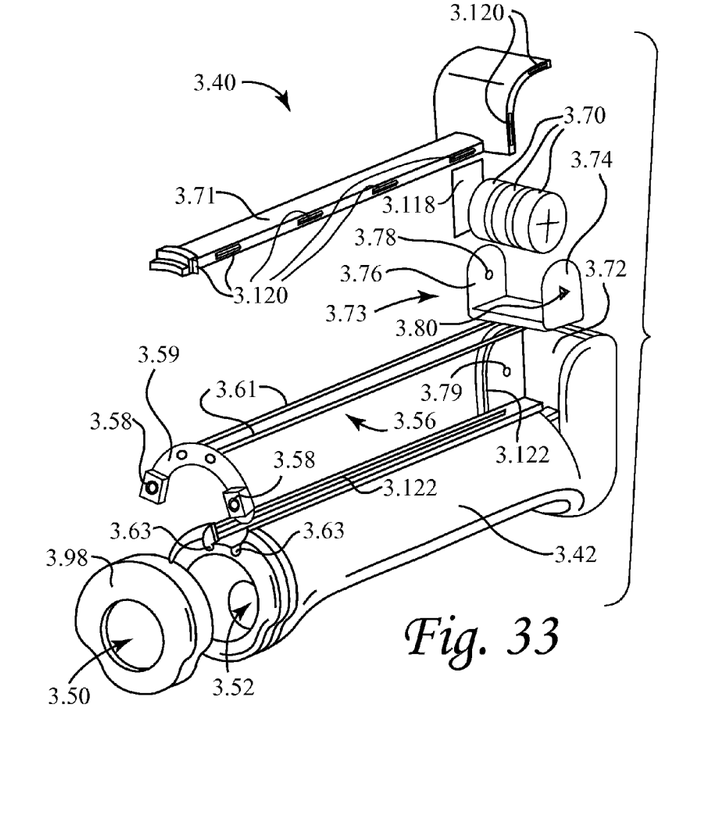
FIG. 33 is an exploded perspective view of the third preferred embodiment of the light of the present invention, showing how the various pieces are assembled together.

Referring especially to FIG. 33, third embodiment 3.40 of the light includes a battery compartment 3.72 that holds a battery holder 3.73 having metallic left and right battery contacts 3.74 and 3.76. It should be noted that right battery contact 3.76 has a small hole 3.78 therethrough in alignment with a similar small access hole 3.79 through the right wall of battery compartment 3.72. The left battery contact 3.74 has an inwardly-bent triangular flap 3.80 that engages the positive ("+") terminal of the leftmost battery 3.70 when all three batteries 3.70 are inserted into the battery holder 3.73. Similar to the second embodiment, an insulating strip 3.118 is interposed between right battery contact 3.76 and rightmost battery 3.70, thereby interrupting the circuit and preventing batteries 3.70 from supplying power to the lamps 3.58. After light 3.40 has been assembled, proper operation of circuit 3.56 can be tested by inserting a conducting metallic needle through hole 3.78 from the outside of battery compartment 3.72, through insulating strip 3.118, and contacting the rightmost battery 3.70, thereby completing the circuit between rightmost battery 3.70 and contact 3.76 and allowing batteries 3.70 to supply power to the lamps 3.58.

As seen in FIG. 33, wires 3.61 carry the current to and from lamps 3.58 via circuit board 3.59, and wires 3.61 are received into longitudinal grooves 3.63 within barrel 3.42. A snap-in circuit cover 3.71, having a plurality of laterally-extending tabs 3.120 that matingly engage channels 3.122 in barrel 3.42, is provided to produce a sealed unit, with insulating strip 3.118 extending out of the battery compartment. A transparent cap 3.98 is then fitted to distal end 3.46 of barrel 3.42 over circuit board 3.59 and LED lamps 3.58.

To illuminate the lamps 3.58 during normal use by a dentist, the dentist simply pulls the insulating strip 3.118 from the battery compartment 3.72 (see dotted line in FIG. 32), thereby permitting battery contact 3.76 to contact rightmost battery 3.70, thereby completing the circuit and causing the battery to power lamps 3.58. Insulating strip 3.118 is thus seen to function as a single-use switch to turn the lamps on during use.

With the exception of electrical circuit 3.56, all parts of third embodiment 3.40 are preferably constructed of a sterilizable plastic so that third embodiment 3.40 can be sterilized, enclosed in a sterile package, opened by the dentist and used, and then discarded after use on a single patient, thereby reducing transmission of germs and diseases between patients. The dentist uses the third embodiment to administer anesthetic just as with the first and second embodiments.

Figures 34, 35:
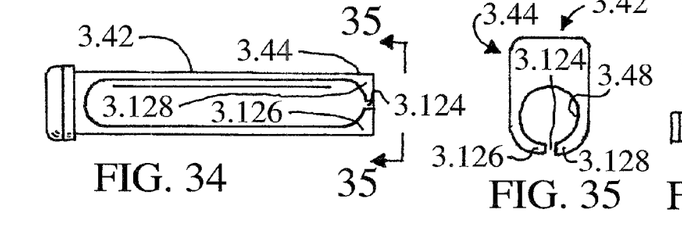
FIG. 34 is a bottom view of an improvement to the third embodiment of the light of the present invention, similar to FIG. 27, and showing the slit in the barrel to accommodate slightly larger syringes.
FIG. 35 is a rear view of the improvement to the third embodiment of the light of the present invention, similar to FIG. 31, and showing the slit in the barrel to accommodate slightly larger syringes.
Figure 36:
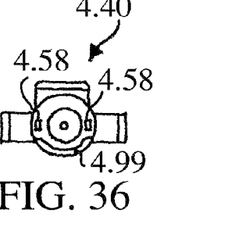
FIG. 36 is a front view of the fourth preferred embodiment of the light of the present invention, taken substantially along the line 36-36 shown in FIG. 37.
Figure 37:
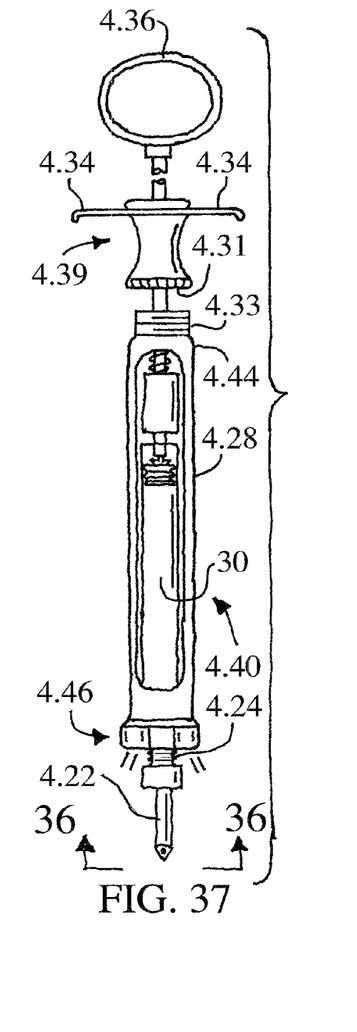
FIG. 37 shows a bottom view of fourth preferred embodiment of the light of the present invention, showing the prior art finger grips and plunger assembly that is threadedly received onto the proximal end of the body and showing attachment of the hypodermic needle to the distal end of the body.
Figure 38:
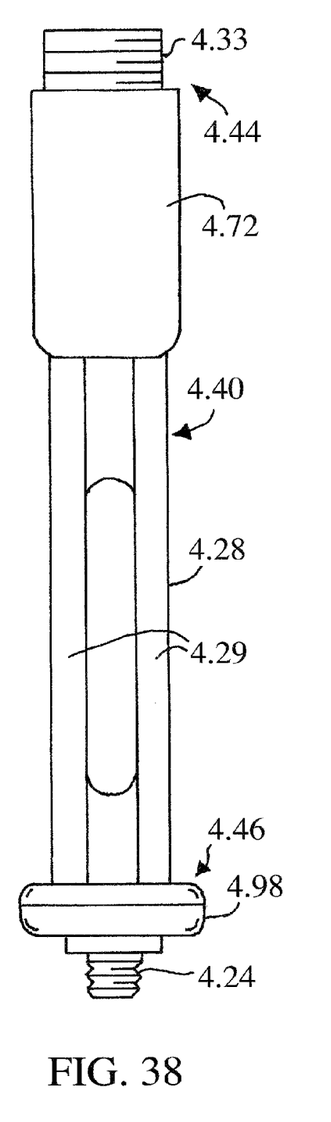
FIG. 38 shows a top view of the fourth preferred embodiment of the light of the present invention, with the prior art finger grips and plunger assembly removed and with the hypodermic needle removed.
Figure 39:
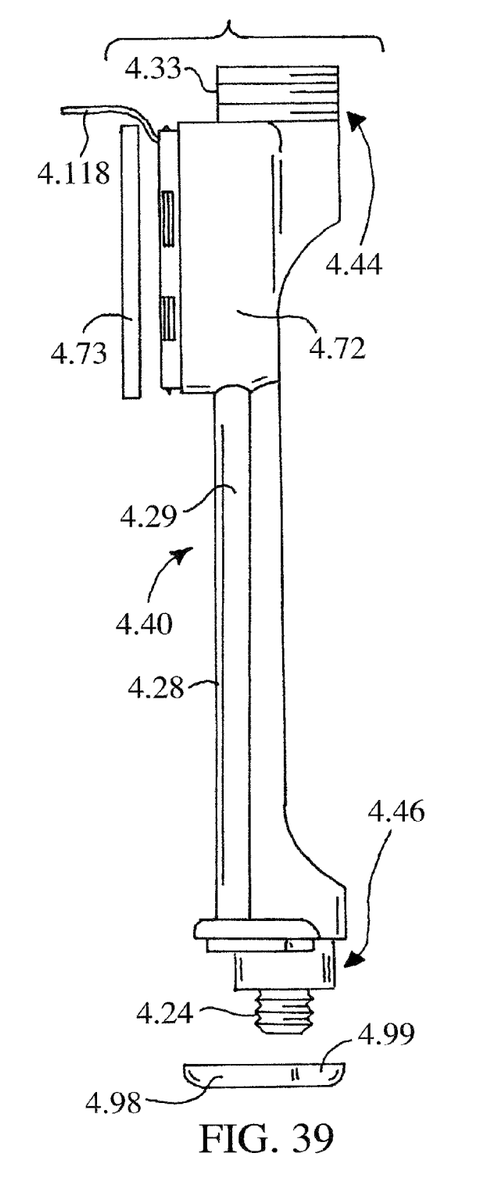
FIG. 39 is a side view of the fourth preferred embodiment of the light of the present invention, with the prior art finger grips and plunger assembly removed and with the hypodermic needle removed, and showing the removable battery compartment cover and the transparent cap at the distal end of the body. The view from the other side is a mirror image of FIG. 39.

Experimental testing of the third embodiment 3.40 with a variety of well-known syringes 20 has shown that there are slight variations in the certain body outer diameter 38 of tubular body 28 of prior art syringe 20, previously described, such that the outer diameter of the tubular body 28 of syringe 20 may be slightly greater than the nominal 10 mm diameter that most syringes from most manufacturers have. To accommodate this variation, a small longitudinal slit 3.124 (see FIGS. 34 and 35) is preferably provided in the proximal end 3.44 of barrel 3.42 so that, when a slightly larger body 28 of a syringe 20 is inserted into first opening 3.48 of barrel 3.42, the slit 3.124 permits the barrel opening 3.42 to expand somewhat because of the resilience of the opposing fingers 3.126, 3.128 that meet proximate slit 3.124 to form opening 3.48.

Referring now to FIGS. 36, 37, 38, 39, and 40, the fourth preferred embodiment 4.40 of the light of the present invention is shown and can now be described. There are many similarities between the fourth embodiment 4.40 and the second and third embodiments 2.40, 3.40, and only the differences will be described in detail, it being understood that similar structural features of the various embodiments perform similar functions. Reference designators for the fourth embodiment have a prefix of "4.", and similar structural features of the first, second, third, and fourth embodiments have the same suffix (e.g., "40", "2.40", "3.40", "4.40", etc.).

Like the second embodiment 2.40, fourth embodiment 4.40 has a threaded fitting 4.24 for receipt of a hypodermic needle 4.22. As with all embodiments, the syringe body 4.28 receives therewith a vial 30 of local anesthetic. Just as with prior art oral anesthesia syringes, embodiment 4.40 includes a thumb-operated plunger 4.36 with finger grips 4.34. Prior art thumb-operated plunger 4.36 with finger grips 4.34 are known to comprise together a finger grip and plunger assembly 4.39 that has a threaded female end 4.31 that is typically threaded onto a mating threaded male portion 4.33 of the proximal end 4.44 of the body 4.28. Because dentists seem to prefer the weighty metal feel of the prior art finger grip and plunger assembly 4.39, the fourth embodiment 4.40 of the present invention provides a similar threaded male portion 4.33 onto which a prior art finger grip and plunger assembly 4.39 may be threadedly received, rather than having the finger grip and plunger assembly be an integral part of the disposable syringe and light combination 2.40 of the second embodiment. Such dentists who prefer to use their weighty finger grip and plunger assembly 4.39 can simply put finger grip and plunger assembly 4.39 into an autoclave or other sterilizing apparatus between patients, and simply discard the rest of the fourth embodiment 4.40 after use on a single patient. It will be noted that the location of battery compartment 4.72 has been moved slightly toward the distal end 4.46 of the body 4.28 as compared with the second embodiment 2.40, so as to accommodate the threaded male portion 4.33. As with the second embodiment 2.40, battery compartment cover or top 4.73 fits over the battery compartment 4.72 with an insulating strip pull tab 4.118 (see the circuit of FIG. 40) extending out of the battery compartment 4.72 just as in the second embodiment, so as permit the dentist to apply power to the LED lamps as described in connection with the operation of the second embodiment.

As another change to the fourth embodiment 4.40 from the second embodiment 2.40, experimental testing has shown that, for a given choice of batteries (such as battery 4.70 of electrical circuit 4.56, hereinafter described), two LEDs 4.58 will have brighter illumination than if three LEDs 4.58 were to be used. The reason for this brighter illumination when two LED lamps are used rather than three LED lamps is that the battery current is source limited, and is powering one fewer LED lamp when only two LED lamps are used. Therefore, the distal end 4.46 of the body 4.28 of the fourth embodiment 4.40 has two LED lamps 4.58, using a structure similar to the distal end 3.46 of the barrel 3.42 of the third embodiment 3.40. As with the third embodiment, the fourth embodiment has a transparent cap 4.98 fitted to the distal end 4.46 of the body 4.28 over a circuit board (not shown, but similar to circuit board 3.59) and the two LED lamps 4.58. Otherwise, the structure of the body of the fourth embodiment is similar to the structure of the body of the second embodiment, and the distal end 4.46 of the fourth embodiment is similar to the structure of the third embodiment. Experimental testing has shown that the reduced radius portion 4.99 of the transparent cap 4.98, also present in the third embodiment (compare FIGS. 28 and 36) provides greater visibility for the dentist of the injection site. When this reduced radius portion 4.99 of the transparent cap 4.98 is combined with the brighter illumination of the LEDs that is present when two, rather than three, LED are used, with the two LEDs encircling the hypodermic needle and being approximately on opposite lateral sides of the needle, the dentist is provided greater illumination of the inside of the patient's mouth and of the injection site, with less obstruction, than has been heretofore possible with the prior art.

Figure 40:
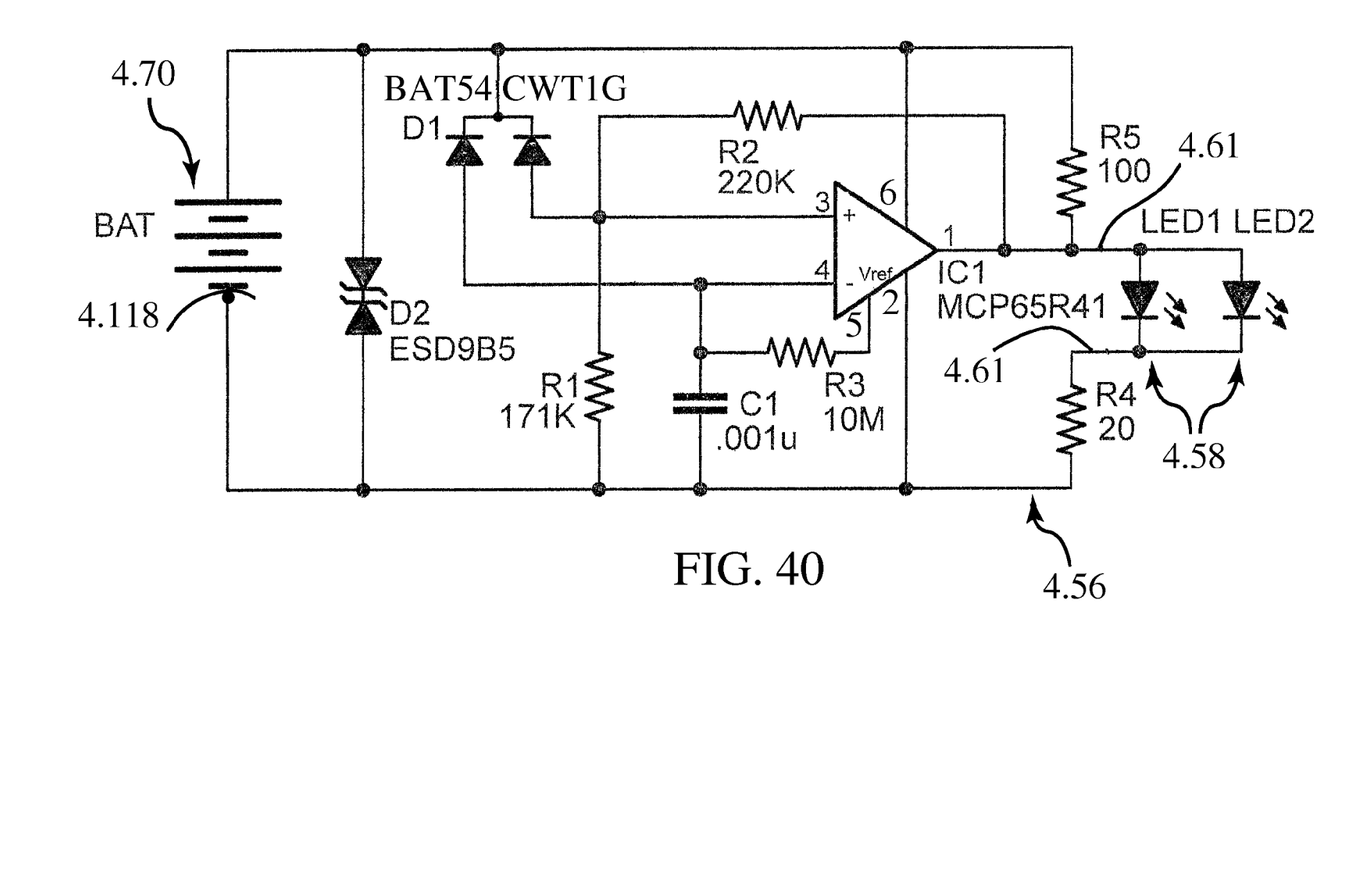
FIG. 40 is a schematic of an improved electrical circuit of the present invention, which can be used in all embodiments.

Referring to FIG. 40, the electrical circuit 4.56 of the present invention can now be described. This circuit is preferably substituted for electrical circuits 2.56 and 3.56 that are used on the second and third embodiments of the present invention, and is also preferably used for the fourth embodiment of the present invention.

Circuit 4.56 positively cuts off and extinguishes any light emitting from the LEDs while ensuring the batteries will continue to drain well past the point of recovery. It is essentially a voltage comparator operating as a current shunt.

Circuit 4.56 is composed primarily of a low power, precision voltage comparator IC1, preferably a well-known MCP65R41 integrated circuit device having an internal 1.2 VDC voltage reference and a totem pole FET output structure. Three button cell batteries, such as Energizer brand 392/384 multi-drain button-cell batteries (also known as SR41 batteries) are used as a power source 4.70 utilizing an insulating strip pull tab 4.118 between one of the batteries and its power contact, as a single use, on-only switch.

IC1 compares the voltage of its positive input at pin 3 to its internal 1.2 VDC reference voltage output which is applied to its negative input at pin 4, delayed slightly at power up by the time constant generated by R3 and C1. At power up, upon removal of the insulating strip pull-tab 4.118, R5 supplies enough battery power to the LEDs 4.58 to establish a voltage greater than 1.2 VDC at pin 3 of IC1 before pin 4 reaches 1.2 VDC.

As long as the input at pin 3 is greater than the 1.2 VDC reference at pin 4, the output of IC1 remains in the High output state, applying battery voltage, less its output FET's forward voltage drop, directly to LEDs 4.58. R4 is selected to limit this current to the drive capability of IC1 at the given voltage, in this case approximately 20 ma.

As LEDs 4.58 burn, battery 4.70 drains and the voltage at pin 3 of IC1 approaches the 1.2 VDC reference at pin 4. The voltage divider at pin 3 established by R1 and R2 sets the trip point at which this occurs with respect to the slowly decreasing output voltage at pin 1, and, at this point, the comparator switches to the Low output state. In the Low output state, IC1 drains the remaining battery capacity through R5 while shunting the current that would flow through LEDs 4.58 and R4, thereby turning off LEDs 4.58 and continuing to drain the battery to ensure that LEDs 4.58 will not turn on again. A large amount of hysteresis is established by the difference between the High and Low output states at pin 1 and the corresponding voltage differential they establish at pin 3 via R1 and R2.

In this particular case, the initial voltage of three silver oxide button cell batteries is approximately 3.9 VDC, and the trip point set by R1 and R2 corresponds to a battery discharge voltage of approximately 3.68 VDC. IC1 has an ability to operate down to 1.8 VDC, which is well below the asymptotic voltage discharge curve of the three silver oxide batteries, approximately 3.3 VDC. As a result, IC1 will continue to discharge and the batteries well beyond their ability to recover and re-illuminate LEDs 4.58.

Common cathode diodes D1 provide over-voltage and Electro-Static Discharge ("ESD") protection for IC1's inputs by clamping the input signals to the batteries' and IC1's positive supply voltage, and Transient Voltage Suppressor D2 provides ESD protection for IC1's supply and the LEDs from any spikes larger than its +/−5.8 V breakdown voltage.

The values of R1 and R2 were selected specifically for use with battery 4.70 (three button cell batteries, such as Energizer brand 392/384 multi-drain button-cell batteries (also known as SR41 batteries)) and a two LED load using SMD PLCC-4 white LEDs for LEDs 4.58. These components were selected to achieve the most compact size and brightest illumination for a 10 minute usage interval.

The discharge characteristics of the 392/384 batteries determines the actual length of usage, as the selection of R1 and R2 sets the point where the output voltage drop triggers the voltage comparator to switch to its Low output state. In this case, values of R1=174K and R2=220K were selected to yield a 10 minute average usage time interval, where the voltage divider ratio of:

$$R1/(R1+R2)=0.4416$$

Alternatively, a voltage divider ratio of 0.4432 could be selected using values of R1=191K and R2=240K to achieve an average usage time interval of 13 minutes with these same batteries and LEDs.

These resistor values selected here are for the individual batteries utilized as sourced from a particular vendor. The optimal resistor values and resulting voltage divider ratio for a 10 minute usage time interval are anticipated to vary slightly for similar batteries if sourced from another vendor, as battery manufacturing quality and consistency are expected to deviate slightly and result in different output discharge curves, a typically unpublished button cell battery characteristic.

D1 has been selected as a low cost, high speed input clamp to V+ for over voltage input protection of IC1. IC1 provides its own internal clamping diodes for negative or under voltage input protection clamping to V−. D1 is present in circuit 4.56 as a precaution of good design practice, and is particularly important when comparators such as these are used as external input line receivers. However, because the inputs of IC1 have no exposure to the extremities of the circuit board or the outside world, these inputs should receive ample protection from the Transient Voltage Suppressor D2, and, as a result, this component may be depopulated from circuit 4.56 for cost savings, unless necessitated by observation of manufacturing defect.

The batteries 4.70 and other components of circuit 4.56, except for LEDs 4.58, are mounted on a printed circuit board (not shown) inside battery compartment 4.72, and wires 4.61 pass from that circuit board to the distal end 4.46 of the body 4.28 of the fourth embodiment 4.40 to another small circuit board (not shown, but similar to circuit board 3.59 of the third embodiment). Wires 4.61 pass through longitudinal bores in lateral cylindrical tubes 4.29 that extend longitudinally along body 4.28.

INDUSTRIAL APPLICABILITY

The light of the present invention has industrial applicability when used with an oral anesthesia injection syringe in that it illuminates the needle and the interior of a patient's mouth during injection of an oral anesthetic. The light is self-contained and unobtrusive and permits "hands free" operation, following the needle as the syringe is moved within the patient's mouth. Disposable single-use embodiments are provided that are pre-sterilized and discarded after use, thereby reducing transmission of germs from one patient to another. The circuit of the present invention has industrial applicability to automatically shut down the illumination of the light after a typical duration of use of about ten minutes, thereby causing the light to be extinguished when placed in a hazards disposal container.

Although the present invention has been described and illustrated with respect to a preferred embodiment and a preferred use therefor, it is not to be so limited since modifications and changes can be made therein which are within the full intended scope of the invention.

We claim:

1. In combination, an oral anesthesia injection syringe having a hypodermic needle extending therefrom and having a tubular body with a certain body outer diameter, and a light, said light comprising:
   (a) a barrel having a proximal end and a distal end, said barrel having a first opening at said proximal end and a second opening at said distal end and a longitudinal passageway through said barrel from said first opening to said second opening, said passageway having a transverse inner diameter larger than said certain body outer diameter; and
   (b) an electrical circuit including:
      i. a plurality of lamps proximate said distal end of said barrel and encircling said second opening;
      ii. a battery received into a compartment of said barrel for powering said plurality of lamps; and
      iii. shut off circuitry interposed between said battery and said plurality of lamps;
   said tubular body of said syringe being received within said passageway with said tubular body of said syringe extending through said first opening and with said needle extending out of said second opening, with said plurality of lamps, when powered by said battery, illuminating said needle and an injection site of said needle; said shutoff circuitry extinguishing the illuminating by said plurality of lamps following an interval of illumination by said plurality of lamps, said shutoff circuitry including a current shunt that engages only after said interval of illumination to drain said battery.

2. The light as recited in claim 1, in which said proximal end of said barrel includes a pair of opposing resilient fingers having a longitudinal slit therebetween into said first opening.

3. The light as recited in claim 1, in which said light is pre-sterilized and disposable after use on a single patient.

4. An oral anesthesia injection syringe having a body, said body having a proximal end and a distal end, said distal end of said syringe being adapted for receipt of a hypodermic needle thereon, said syringe including an electrical circuit integral therewith, said electrical circuit including:
   (a) a plurality of lamps proximate said distal end of said body and encircling said hypodermic needle when said needle is received on said distal end; and
   (b) a battery received into a compartment of said body for powering said plurality of lamps; and
   (c) shut off circuitry interposed between said battery and said plurality of lamps;
   said plurality of lamps, when powered by said battery, illuminating said needle when said needle is received on said distal end and illuminating an injection site of said needle; said shutoff circuitry extinguishing the illuminating by said plurality of lamps following an interval of illumination by said plurality of lamps, said shutoff circuitry including a current shunt that engages only after said interval of illumination to drain said battery.

5. The syringe as recited in claim 4, in which said syringe is pre-sterilized and disposable after use on a single patient.

* * * * *